United States Patent [19]

Toriyama et al.

[11] 4,293,698
[45] Oct. 6, 1981

[54] COMPOUND FOR CONTROLLING DIELECTRIC CONSTANT OF LIQUID CRYSTAL

[75] Inventors: Kazuhisa Toriyama, Mobara; Tsujiaki Hata, Yokohama; Shinji Hasegawa; Ken Sasaki, both of Mobara, all of Japan

[73] Assignee: Hitachi, Ltd., Tokyo, Japan

[21] Appl. No.: 111,104

[22] Filed: Jan. 10, 1980

[30] Foreign Application Priority Data

Jan. 12, 1979 [JP] Japan .................................. 54-1351

[51] Int. Cl.$^3$ ...................... C09K 3/34; G02F 1/13; C07D 213/02
[52] U.S. Cl. ...................... 546/301; 252/299.61; 252/408; 350/350 R; 546/290
[58] Field of Search .................. 546/290, 298, 301; 252/299, 408, 63.7; 350/350 R

[56] References Cited

U.S. PATENT DOCUMENTS

| | | | |
|---|---|---|---|
| 3,923,857 | 12/1975 | Boller et al. | 252/299 |
| 3,927,064 | 12/1975 | Boller et al. | 252/299 |
| 3,983,049 | 9/1976 | Aftergut et al. | 252/299 |
| 4,027,950 | 6/1977 | Moriyama et al. | 252/299 |
| 4,122,026 | 10/1978 | Osmam | 252/299 |

OTHER PUBLICATIONS

Pudziamowski, A. T., et al., Mol. Cryst. Liq. Cryst., vol. 34 (Letters), pp. 33-42 (1976).
Barbarin, F., et al., Mol. Cryst. Liq. Cryst., vol. 39, pp. 199-215 (1977).
Barbarin, F., et al., Mol. Cryst. Liq. Cryst., vol. 39, pp. 217-228 (1977).

*Primary Examiner*—Teddy S. Gron
*Attorney, Agent, or Firm*—Charles E. Pfund

[57] ABSTRACT

There is provided a compound for controlling dielectric constant of liquid crystal consisting of 4-p-Alkylbenzoyloxypyridine oxide represented by the general formula

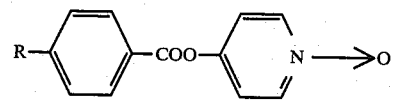

where R is a normal alkyl group having 1 to 9 carbon atoms.

10 Claims, No Drawings

COMPOUND FOR CONTROLLING DIELECTRIC CONSTANT OF LIQUID CRYSTAL

BACKGROUND OF THE INVENTION

The present invention relates to a compound for controlling the dielectric constant of liquid crystal and, more particularly, to a compound to be added to such a liquid crystal as a nematic liquid crystal which is used for an electrooptical display device so as to drive said display device by low driving voltage.

A typical liquid crystal display cell is the Field Effect Mode (hereinafter called as F.E.M.) cell proposed by M. Schadt et al (Applied Physics Letters, 18, 127–128 (1971). This F.E.M. cell comprises two transparent electrode plates arranged opposedly and nematic liquid crystal having positive of dielectric anistropy filled between said two electrodes, wherein longitudinal axes of molecules of said liquid crystal being parallel to said electrodes and being twisted in herical arrangement by a predetermined angle between said electrodes, thereby imparting a predetermined rotatory capacity for incident rays. When the voltage is applied on the electrode plates, these liquid molecules become vertically arranged of their longitudinal axes in respect of the electrode plates, thereby causing the rotatory capacity to disappear. This change in the rotatory capacity is converted to the change of optical transmittancy of the cell by utilizing a polarizer so as to enable displays.

However, a recent display device utilizing the F.E.M. cell requires such a relatively high driving voltage as 3 volts. Accordingly, in order to use small driving battery and to decrease the driving electric power for the display device, various kinds of method for driving the display device by a driving voltage lower than 3 volts have been researched and developed. In order to enable the low voltage driving of F.E.M. cells, the anisotropy of dielectric constant for the nematic liquid crystals to be filled in the cell is controlled to be at a certain positive value above a predetermined value, thereby lowering the threshold voltage for the said nematic liquid crystals as much as possible. For this purpose, it is preferable to use an addition compound for controlling an anisotropy of dielectric constant of liquid crystal and more particularly to utilize a large positive anisotropy of dielectric constant. By adding such a compound, it becomes possible to use the nematic liquid crystal having a negative or a comparative small anisotropy of dielectric constant for F.E.M. cells, and low voltage driving becomes also possible. In this case, the compound, which is added to the liquid crystal, for controlling the dielectric constant thereof is required essentially to have the following properties (1) to (5).

(1) The anisotropy of dielectric constant of the compound should be of an extremely large positive value;

(2) The compound dissolves well in various nematic liquid crystals, does not separate or deposit when left at low temperature and does not increase viscosity of nematic liquid crystal;

(3) The compound does not radically decrease the temperature range for the nematic liquid crystal, nor shift to the high temperature side;

(4) The compound does not disturb the ordered orientation of molecular structure of the nematic liquid crystal;

(5) The compound has excellent chemical stability, and does not decompose by water, light, heat, etc.

Many effective compounds have been known heretofore as compounds for controlling dielectric constant which include 4-substituted benzoic acid-4′-cyanophenyl ester (Japanese Patent Publication No. 52-2902), 4-substituted bensylideneamino-4′-cyano aniline (Japanese Patent Publication No. 52-942) and 4, 4′-disubstituted biphenyl (Japanese Laid Open Publication No. 49-95882). However, none of these known compounds satisfies all the properties listed above. 4-substituted benzoic acid-4′-cyanophenyl ester, for example, is inferior in respect to said property (2) and the first half of said property (3) and, at the same time, 4-substituted benzylideneamino-4′-cyano aniline is inferior in respect to said property (5), especially the property against water. Moreover, 4, 4′-disubstituted biphenyl is also inferior in respect to said properties (1) and (2).

SUMMARY OF THE INVENTION

The object of the present invention, therefore, is to provide a compound for controlling dielectric constant of liquid crystal which is sufficiently provided with all of those properties listed under said (1) to (5).

The inventors of this invention have designed and synthesized a compound, namely 4-p-alkylbenzoyloxypyridine, represented by the general formula

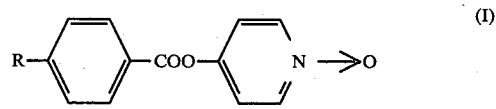

(wherein R is a normal alkyl group having 1 to 9 carbon atoms) in order to achieve the object of the invention as above explained.

Detailed description of 4-p-alkylbenzoyloxypyridine oxide in accordance with the present invention is now given.

DESCRIPTION OF THE PREFERRED EMBODIMENT

The compound represented by the formula (I) is prepared by the following method.

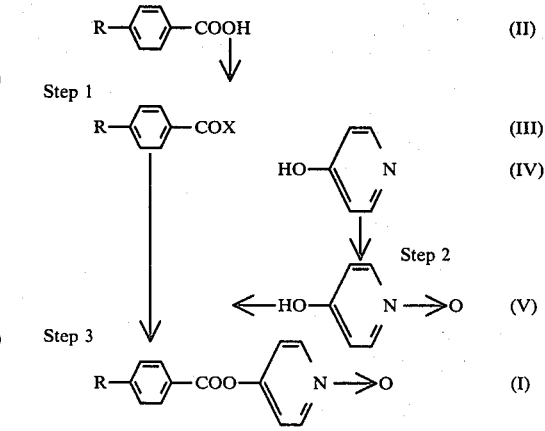

Step 1: The compound of the formula (II) (wherein R has the same meaning as above, and this applies hereinafter.) is reacted with halogenating agent to obtain the compound of the formula (III) (wherein X is a halogen atom). In this case, X preferred in the compound of the formula (III) is a chlorine atom, and thionyl chloride is preferably used as a halogenating agent. The reaction is carried out under normal pressure and at a reflux temperature of the reaction mixture. After the reaction has been completed, the excess halogenating agent is removed to be used for the reaction in the Step 3.

Step 2: The compound of the formula (IV) is oxidized to obtain the compound of the formula (V). The reaction is carried out under a normal pressure, and the resulting compound of the formula (V) is recrystallized by ethanol for further refining. In this case, the melting point of the compound of the formula (V) thus refined is 241° C.

Step 3: The compound of the formula (III) refined in the Step 1 and the compound of the formula (V) are reacted in the inactive organic solvent. In this case, diethyl ether, tetrahydrofuran, dimethylformamide, benzene cyclohexane, or carbon tetrachloride may be used as inactive organic solvent. Although the compound of the formula (V) does not dissolve in diethyl ether or benzene, it becomes easily dissolved with the compound of the formula (I) when it is used in dispersion. Thus the solution becomes transparent. In order to remove hydrogen halide freed during the reaction from the reaction system, it is preferable to include basic substance such as pyridine or tertiary amine. The reaction is carried out under the normal pressure, and within the temperature range ranging from the room temperature to the reflux temperature of the reaction mixture. By subjecting the reaction product to solvent extraction, washing with water, drying and refining, the compound of the formula (I) which is the aimed product of this invention is isolated.

Table 1 lists the physical properties of the compound of the formula (I) prepared in the above described manner.

TABLE 1

R—⟨phenyl⟩—COO—⟨phenyl⟩—N→O

| No. | R | m.p. (°C.) |
|---|---|---|
| 1 | $CH_3$ | 85° C. |
| 2 | $C_2H_5$ | 106° C. |
| 3 | $n-C_3H_7$ | 93° C. |
| 4 | $n-C_4H_9$ | 112° C. |
| 5 | $n-C_5H_{11}$ | 99° C. |

TABLE 1-continued

R—⟨phenyl⟩—COO—⟨phenyl⟩—N→O

| No. | R | m.p. (°C.) |
|---|---|---|
| 6 | $n-C_6H_{13}$ | 118° C. |
| 7 | $n-C_7H_{15}$ | 100° C. |
| 8 | $n-C_8H_{17}$ | 125° C. |
| 9 | $n-C_9H_{19}$ | 112° C. |

(The m.p. stands for melting point.)

The compound of the formula (I) obtained in the above mentioned manner acts effectively as dielectric constant control for all type of nematic liquid crystals. Accordingly, it is possible to use the compound of the formula (I) combined with any types of nematic liquid crystals. For instance, the composition obtained by mixing the compound of the formula (I) with such nematic liquid crystals as 4, 4'-disubstituted benzoic acid phenyl ester, 4, 4'-disubstituted benzoic acid thiophenyl ester, 4, 4'-disubstituted benzylideneaniline, 4, 4'-disubstituted biphenyl, 4, 4'-disubstituted cyclohexane carboxylic acid phenyl ester or 4, 4'-disubstituted biphenyl cyclohexane presents preferred properties as liquid crystals to be used with F.E.M. cells. In this case, the mixing ratio of the compound of the formula (I) may be set arbitrarily, but generally speaking, the ratio of 5 to 30% based on the sum of the nematic liquid crystal and the compound of the formula (I) is recommended.

Tables 2 and 3 lists the nematic liquid crystal compositions containing the compound of the formula (I). The physical and electrooptical properties are also described in the tables. In the column for transition temperatures in the tables, C denotes solid phase, N nematic phase, and I isotropic liquid phase, and in the column for nematic liquid crystal compositions the numbers 1 to 9 represent the same compounds as listed in Table 1.

Liquid crystal cell obtainable by filling the sample into F.E.M. cell where the liquid crystal layer thickness is 10 um was used to measure the threshold voltage. The threshold voltage used was taken when the transmittancy is 90% as a variable voltage of |1 KHz sin| wave is applied on the liquid crystal cell. The transmittancy when no voltage is applied is held as 100% as a reference for measuring the transmittancy of the light (%), and that when the light from the source is completely shut off as 0.

TABLE 2

| | | Transition temperature (°C.) | | Threshold voltage |
|---|---|---|---|---|
| | | C → N | N ⇌ I | (V) at 25° C. |
| Nematic liquid crystal (A) | $CH_3O$—⟨phenyl⟩—N=N(O)—⟨phenyl⟩—$nC_4H_9$ (65 mol %) | −5 | 75 | — |
| | $CH_3O$—⟨phenyl⟩—N=N(O)—⟨phenyl⟩—$C_2H_5$ (35 mol %) | | | |
| Nematic A liquid crystal composition containing compound of | (90 mol %) + 1 (10 mol %) | −6 | 58 | 1.40 |
| | (90 mol %) + 2 (10 mol %) | −8 | 60 | 1.45 |
| | (90 mol %) + 3 (10 mol %) | −5 | 60 | 1.43 |
| | (90 mol %) + 4 (10 mol %) | −10 | 65 | 1.45 |
| | (90 mol %) + 5 (10 mol %) | −6 | 62 | 1.40 |
| | (90 mol %) + 6 (10 mol %) | −10 | 68 | 1.38 |
| | (90 mol %) + 7 (10 mol %) | −10 | 64 | 1.36 |

TABLE 2-continued

|  |  | Transition temperature (°C.) C → N | N ⇌ I | Threshold voltage (V) at 25° C. |
|---|---|---|---|---|
| formula (I) | (90 mol %) + 8 (10 mol %) | −8 | 68 | 1.38 |
|  | (90 mol %) + 9 (10 mol %) | −4 | 66 | 1.40 |

TABLE 3

|  |  | Transition temperature (°C.) C → N | N ⇌ I | Threshold voltage (V) at 25° C. |
|---|---|---|---|---|
| Ester type nematic liquid crystal TN 103 |  | −20 | 82 | 1.65 |
| Nematic liquid crystal comoposition containing compound of formula (I) | TN103(95 mol %) + 1 (5 mol %) | −16 | 68 | 1.22 |
|  | " + 2 (5 mol %) | −20 | 70 | 1.22 |
|  | " + 3 (5 mol %) | −16 | 74 | 1.24 |
|  | " + 4 (5 mol %) | −20 | 72 | 1.26 |
|  | " + 5 (5 mol %) | −18 | 74 | 1.23 |
|  | " + 6 (5 mol %) | −20 | 73 | 1.26 |
|  | " + 7 (5 mol %) | −20 | 82 | 1.30 |
|  | " + 8 (5 mol %) | −21 | 76 | 1.36 |
|  | " + 9 (5 mol %) | −20 | 82 | 1.40 |

Because the anisotropy of dielectric constant for the nematic liquid crystal (A) listed in Table 2 is negative, it cannot be used with F.E.M. cell without modification. As is clear from the results disclosed in Tables 2 and 3, addition of the compound of the formula (I) in a small amount will make such a use possible. The material which has a low threshold voltage, which is applicable to F.E.M. cell presently, which has a large anisotropic value of dielectric contant and which has a low threshold voltage is a nematic material of ester group. By adding the compound of the formula (I), a very low threshold voltage value heretofore unobtainable is obtained and the transition temperature change is also quite slight.

As mentioned above, 4-p-alkylbenzolyloxypyridine oxide according to the present invention realized lowering the threshold voltage value of the nematic liquid crystal by a radical degree without changing the transition temperature (N⇌I) when compared to the conventionally known compounds. The present invention is further explained concretely in respect of manufacturing the starting material and the example.

EXAMPLE 1 OF THE STARTING MATERIAL

To 17.8 g. (0.10 mol) of the compound of the formula

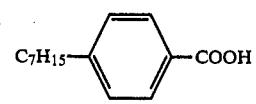

is introduced 100 ml. of thionyl chloride, and after resultant mixture is refluxed for 30 minutes, excess thionyl chloride is distilled off.

To the resultant reaction product is added 11.1 g. (0.10 mol) of the compound represented by the formula

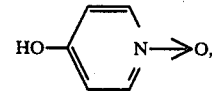

150 ml. of cyclohexane, and 10 g. of pyridine, and the mixture is reacted for 2 hours with stirring at a room temperature. The reaction liquid is then washed with 1% hydrochloric acid and water, and cyclohexane is distilled off from the reaction liquid. The obtained product is passed through a sylica gel column, and recrystallized by isopropyl alcohol to obtain 19.5 g of

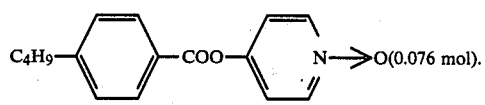

The yield was 76%. Elemental analysis of

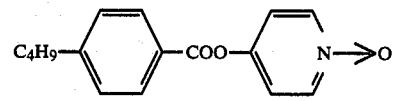

was the same as the result of calculation.

EXAMPLE 2

To 13.6 g (0.10 mol) of the compound having the formula

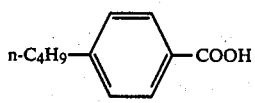

was reacted in the manner similar to that of Example 1 with thionyl chloride, and the resultant compound was reacted with

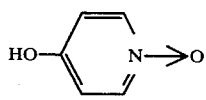

similarly as in the Example 1, and recrystallized from isopropyl alcohol to obtain 22.5 g of

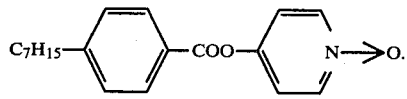

The yield was 72%. In this case, the elemental analysis showed the same values as those obtained by calculation.

What is claimed is:

1. A compound for controlling the dielectric constant of liquid crystals consisting of a 4-p-Alkylbenzoyloxypyridine oxide represented by the general formula

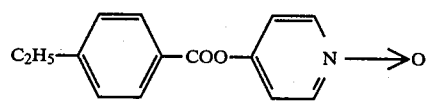

wherein R is a normal alkyl group having 1 to 9 carbon atoms.

2. A compound for controlling the dielectric constant of liquid crystals according to claim 1 wherein the said formula may be expressed as

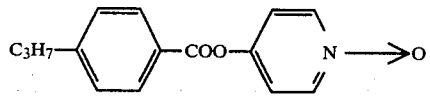

3. A compound for controlling the dielectric constant of liquid crystals according to claim 1 wherein the said formula may be expressed as

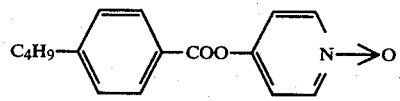

4. A compound for controlling the dielectric constant of liquid crystals according to claim 1 wherein the said formula may be expressed as 5. A compound for controlling the dielectric constant of liquid crystals according to claim 1 wherein the said formula may be expressed as

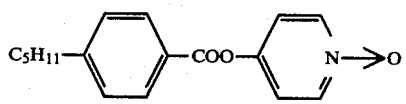

6. A compound for controlling the dielectric constant of liquid crystals according to claim 1 wherein the said formula may be expressed as

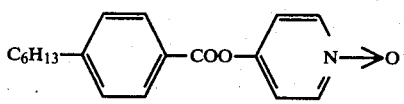

7. A compound for controlling the dielectric constant of liquid crystals according to claim 1 wherein the said formula may be expressed as

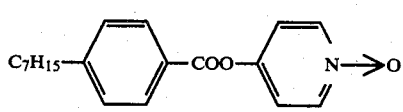

8. A compound for controlling the dielectric constant of liquid crystals according to claim 1 wherein the said formula may be expressed as

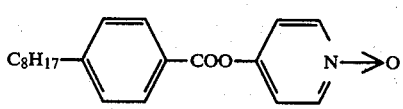

9. A compound for controlling the dielectric constant of liquid crystals according to claim 1 wherein the said formula may be expressed as

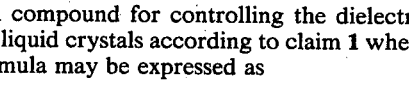

10. A compound for controlling the dielectric constant of liquid crystals according to claim 1 wherein the said formula may be expressed as

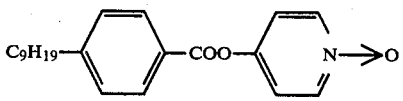

* * * * *